United States Patent [19]

Levadoux et al.

[11] Patent Number: 5,843,765

[45] Date of Patent: Dec. 1, 1998

[54] STREPTOMYCES MICROORGANISM USEFUL FOR THE PREPARATION OF (R)-BACLOFEN FROM THE RACEMIC MIXTURE

[75] Inventors: Wayne Levadoux, Ville St-Laurent; Denis Groleau, Duvernay; Michael Trani, Lasalle; Robert Lortie, Outremont, all of Canada

[73] Assignee: National Research Council of Canada, Ottawa, Canada

[21] Appl. No.: 791,952

[22] Filed: Jan. 31, 1997

[51] Int. Cl.⁶ ..................................................... C07C 00/00
[52] U.S. Cl. ........................... 435/280; 435/885; 435/902
[58] Field of Search ..................................... 435/280, 885, 435/902

[56] References Cited

U.S. PATENT DOCUMENTS 4,204,044  5/1980  Suhara et al. ............................ 435/280
5,108,917  4/1992  Bertola et al. ........................... 435/136
5,302,528  4/1994  Battistel et al. ......................... 435/280

*Primary Examiner*—David A. Redding
*Attorney, Agent, or Firm*—J. Wayne Anderson

[57] ABSTRACT

The invention disclosed relates to the biological production of substantially isomerically pure (R)-baclofen and structurally related compounds, from the racemic mixture of (R)- and (S)-isomers thereof, and to the isolation of a Streptomyces microorganism from Nature which is capable of preferentially metabolizing one of the isomers while showing minimal metabolic activity on the other isomer. A fermentation or bioconversion process using this microorganism or the cell-free enzymes derived therefrom for the biological resolution of a racemic mixture of (R)- and (S)-baclofen and structurally related compounds is also disclosed.

15 Claims, 7 Drawing Sheets

STREPTOMYCES MICROORGANISM USEFUL FOR THE PREPARATION OF (R)-BACLOFEN FROM THE RACEMIC MIXTURE

BACKGROUND OF THE INVENTION

This invention relates to the production of substantially isomerically pure (R)(−)-baclofen and structurally related compounds, by means of selective microbial degradation. For example, (R)(−)-baclofen can be isolated from a racemic mixture of (R)- and (S)-baclofen. The invention also relates to the microorganism used in the process.

(R)-baclofen (Formula I below) is an antispastic drug, analog to the neurotransmitter γ(gamma)-aminobutyric acid (GABA). Baclofen as a drug consists of two isomers, the (R)-(−)-isomer and the (S)-(+)-isomer. It is known that the (R)-isomer (I) is the active one and patients would greatly benefit from the administration of enantiomerically pure (R)-baclofen, even though the (R)-isomer is also responsible for the toxic and other side effects. This comes from the fact that (S)-baclofen is antagonistic to the (R)-form and its presence makes it necessary to administer higher baclofen doses (*J. of Liquid Chromatogr.* 16(15):3311–3320, 1993).

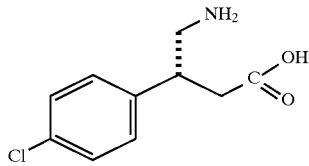

DESCRIPTION OF THE PRIOR ART

Pure (R)-baclofen can be obtained through stereoselective synthesis (Chenevert, R. and Desjardins, M., *Can. J Chem.* 72, 2312–2317 (1994); Schoenfelder, A. et al. *Synlett* 7 63–64 (1993); Herdeis, C. and Hubmann, H. P., *Tetrahedron Asymm.* 3, 1213–1221 (1992); Hubmann, H. P. and Herdeis, C., German Patent DE 4224342 A1, Jan. 1, 1994) or via chromatographic separation from a racemic mixture (Vaccher, C., *J. of Chromatogr.* 542, 502–507 (1991)).

Microorganisms can show stereoselectivity in the transformation of various chemicals. For instance, different Clostridium strains showed stereoselectivity in the reduction of a β(beta)-keto ester (Christen, M. et al. *J. Chem. Soc. Perkin Trans.* 1, 491–493 (1992)), various strains of Pseudomonas preferentially formed (R)-acetylmandelic acid from O-acetylmandelonitrile (Layh, N. et al. *Arch. Microbiol.* 158, 405–411 (1992)), the fungus *Geotrichum candidum* IFO 5767 can convert racemic 1-arylethanols into corresponding and almost pure (R)-1-arylethanols (Nakamura, K., *Tetrahedron Lett.* 36, 6263–6266 (1995)). It has also been shown that *Rhodococcus rhodochrous* PB1 uses the enantiomers of 3-phenylbutyric acid via two different metabolic pathways (Simoni, S. et al., *Appl. Environ. Microbiol.*, 62, 749–755 (1996)).

Because of the high costs associated with large-scale stereospecific synthesis and chiral chromatography, and also because of the promises offered by microorganisms in regard to stereospecificity, it was decided to look for the presence of microorganisms in Nature which could be used later for the development of a microbial and/or enzymatic bioprocess capable of yielding (R)-baclofen starting from the racemic mixture.

Another prior art reference, U.S. Pat. No. 5,302,528 is directed to resolution of similar racemic carboxylic acid esters, with *Brevibacterium imperiale*.

SUMMARY OF THE INVENTION

It is an object of the invention to isolate and characterize a microorganism (bacterium) from Nature which preferentially metabolizes one of the enantiomers in a racemic mixture, leaving the other substantially unreacted.

It is another object of the present invention to isolate and characterize a microorganism (bacterium) from Nature which preferentially metabolizes (S)-baclofen while showing little or no activity on (R)-baclofen.

It is yet another object of the present invention to use this microorganism in the development of a fermentation bioprocess which yields at the end substantially pure (R)-baclofen starting from a racemic mixture of (R)- and (S)-baclofen.

According to one aspect of the invention a process for the production of a substantially isomerically pure isomer of a compound of structural formula II

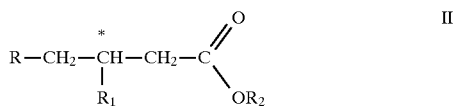

wherein R is $NH_2$ or substituted $NH_2$, $R_1$ is phenyl or p-halo substituted phenyl, $R_2$ is H lower-alkyl, $NH_2$, Cl, or a metal salt thereof and C* is a chiral carbon, is provided, comprising contacting a racemic mixture of the (R)- and (S)-isomers of a compound of formula II, with a biologically purified microorganism identified by ATCC Deposit Accession No. 55794 or the cell-free enzymes derived therefrom, in a suitable aqueous culture medium, to selectively metabolize one of the isomers, while having minimal activity on the other isomer, and recovering the substantially isomerically pure unreacted isomer.

For example, the prior art indicates that the $NH_2$ group can be substituted by forming acid addition salts such as the hydrochloride. Other substituents such as boc (tert-butoxycarbonyl) are also contemplated. Also, $R_1$ can be p-chloro-substituted phenyl (baclofen) or other halogens e.g. the fluro derivative.

The preferred reaction conditions include (a) pH between 5.5 and 7.5; (b) temperature between 20° and 35° C.; (c) source of readily available energy present such as glucose and yeast extract; (d) repeated addition of about 4 g/L of glucose and about 2 g/L of yeast extract greatly favoured the accumulation of (R)-baclofen with an enantiomeric excess (e.e.) greater than 90%.

According to another aspect of the invention, a process is provided for the resolution of racemic baclofen (and related compounds, derivatives, etc), comprising contacting racemic baclofen containing the (R)- and (S)- baclofen with a microorganism or enzymes derived from the microorganism which selectively metabolizes (S)-baclofen, while having substantially no metabolic activity on (R)-baclofen, and recovering the (R)-baclofen.

According to yet another aspect of the invention, a biologically purified culture of the microorganism belonging to the genus Streptomyces, deposited under the Budapest Treaty with the American Type Culture Collection (ATCC) ,Rockville, Md., 20852, USA, on 19 Jun., 1996 under Accession no. 557947 or enzymes derived therefrom, is also provided. The microorganism deposited has been identified as *Streptomyces halstedii olivaceus* strain no. 39, after fatty acid analysis and as *Streptomyces setonii* after 16 S ribosomal analysis. Since ribosomal analysis is generally more accurate, the microorganism is tentatively identified as *Streptomyces setonii*. Viability of the culture cited above was tested and found viable by the ATCC, on 24 Jun., 1996.

It will be appreciated by those skilled in the art that this microorganism and/or its enzymes could be employed for the development of second generation-bioprocesses meeting industry's needs.

It will also be appreciated that both the bacteria and the enzymes can be used immobilized on suitable substrates of various kinds, such as on a gel, in accordance with known art, to increase their stability and facilitate recovery and re-use.

DESCRIPTION OF THE PREFERRED EMBODIMENTS

Figure 1:
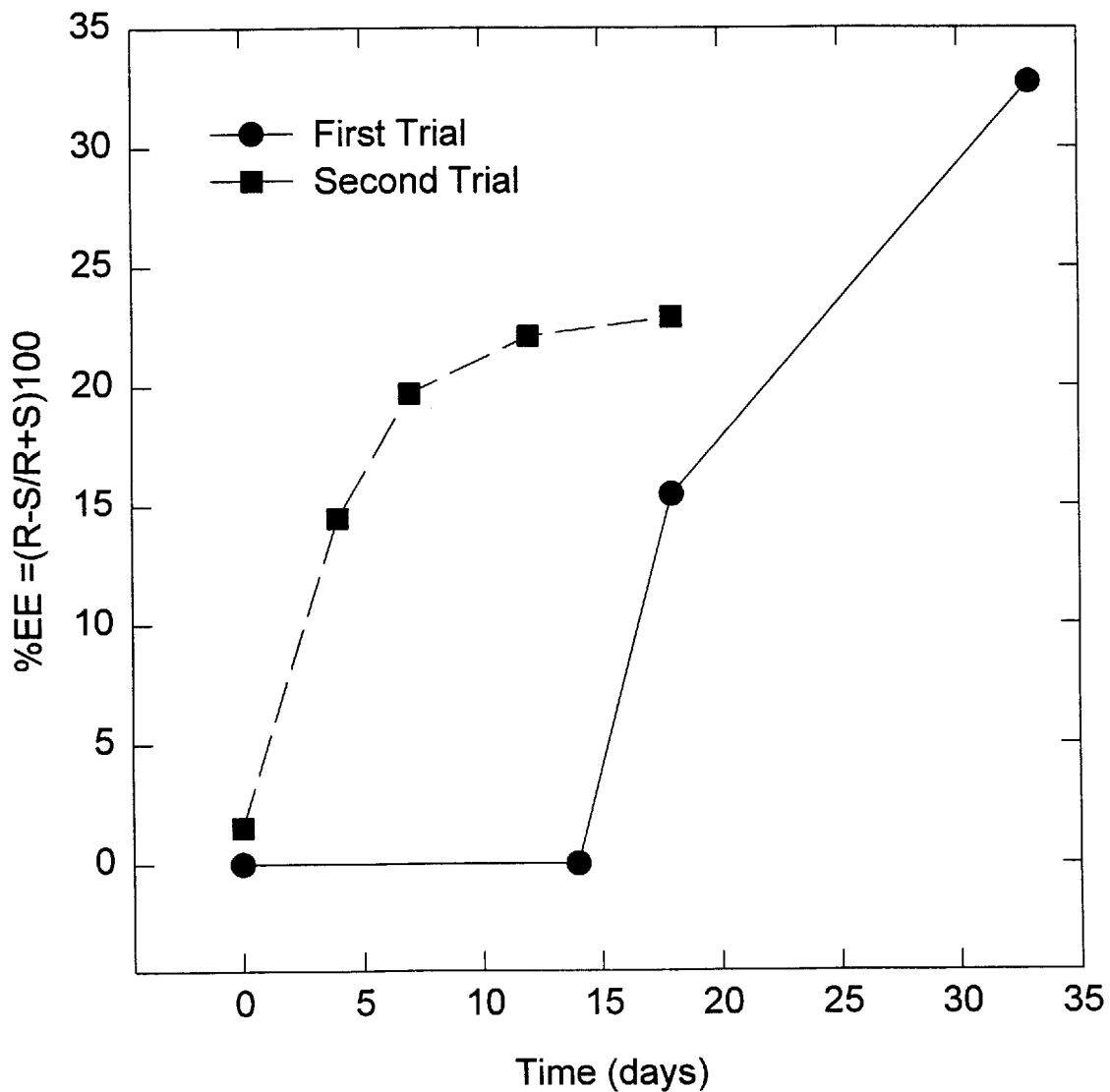
FIG. 1 is a graph illustrating the enrichment in (R)-baclofen during growth of bacterial strain #39 in medium containing racemic baclofen.

The microorganism (bacterium) was obtained from Nature as follows. Fifteen soil samples, originating from various regions of Canada and showing gross differences in appearance and composition, were screened for the presence of microorganisms able to grow in a suitable culture medium containing only water, minerals and racemic baclofen as the sole added carbon and energy source (plus agar whenever required). The composition of the medium is given in Table 1. The isolation of microorganisms was done using two different approaches: (1) dilution of the soil samples and direct plating onto solid medium containing racemic baclofen at a concentration varying from 0.1 to 1 g/L; (2) enrichment cultivation, in the presence of added racemic baclofen at a concentration varying from 0.1 to 2 g/L, of the desired microorganisms possibly present in the soil samples to increase their population before culture isolation. These two approaches are described in more detail below.

Culture isolation using the direct plating approach was done as follows. Serial dilutions of the soil samples were made in sterile deionized water and aliquots of the dilutions $10^{-3}$ to $10^{-6}$ were spread onto solid medium containing racemic baclofen. The plates were incubated at 30° C. for periods up to 6 weeks and examined regularly. Resulting colonies were then transferred onto fresh plates containing racemic baclofen until culture purity was confirmed. The resulting cultures were presumed to metabolize baclofen.

Culture isolation using the enrichment cultivation approach was done as follows. Soil samples were added, in the ratio of one part of soil to nine parts of medium, to Erlenmeyer flasks containing sterile medium with racemic baclofen. The culture medium was similar to that used above for the direct plating approach. The flasks were incubated at 30° C. for up to six weeks and sampled regularly to evaluate microbial growth (microscopy) and to test for the presence of baclofen-metabolizing microorganisms. Resulting colonies were then handled as described above until culture purity was confirmed.

A total of 218 potential baclofen-metabolizing cultures was finally obtained after having used the two above approaches. Based on growth characteristics, each one of the 218 cultures were selected for the next round of tests. Each culture was tested for growth on (R)-baclofen and on (R,S)-baclofen (racemate). It was assumed that growth on (R,S)-baclofen and absence of growth on (R)-baclofen would be presumptive evidence of a culture metabolizing (S)-baclofen selectively. Thirty or so promising cultures were obtained; some of the cultures also showed some growth on (R)-baclofen. The thirty or so promising cultures were, thereafter, tested in shake flask experiments for their ability to selectively metabolize (S)-baclofen starting from the racemic mixture. Two promising cultures were identified. Further investigations showed that one of these two cultures, designated strain #39, was the most suitable candidate for process development.

Process development work was continued with strain #39. Various shake flask experiments were conducted at 30° C. to evaluate the stereoselectivity of strain #39 towards the two isomers of baclofen. In these experiments, strain #39 (inoculum) was added to shake flasks containing defined medium (Table 1) with baclofen at an initial concentration of 0.25 g/L. After nine days of incubation at 30° C., glucose and yeast extracts were added at a final concentration of 4 and 2 g/L, respectively. This was done to improve growth and baclofen metabolism. Initial results confirmed that strain #39 was preferentially metabolizing (S)-baclofen. After 18 days of incubation, the enantiomeric excess (e.e.) of (R)-baclofen over (S)-baclofen attained values over 30%. This confirmed the potential of strain #39 for baclofen resolution.

TABLE 1

Composition of the culture medium used.

| Ingredient | Concentration (per liter) |
|---|---|
| $NH_4Cl$ | 0.5 g |
| $KH_2PO_4$ | 0.54 g |
| $K_2HPO_4$ | 0.7 g |
| $MgSO_4.7H_2O$ | 1.0 g |
| $CaCl_2.2H_2O$ | 0.2 g |
| $FeSO_4.7H_2O$ | 4 mg |
| $MnCl_2.4H_2O$ | 30 µg |
| $ZnCl_2.2H_2O$ | 100 µg |
| $CuCl_2.2H_2O$ | 10 µg |
| $NiCl_2.6H_2O$ | 20 µg |
| $Na_2MoO_4.2H_2O$ | 60 mg |
| $COCl_2.6H_2O$ | 200 µg |
| $H_3BO_3$ | 300 µg |
| baclofen | 0.1 to 2.0 g |
| NOBLE Agar (+/−) | 15 g |

Note: For some fermentor experiments, initial baclofen concentration was 0.25 g/L. In addition, the culture medium used for experiments in fermentors contained glucose (4 g/L) and yeast extract (2 g/L).

The results of microscopic observations and of Gram staining indicated that strain #39 is a Gram-positive bacterium probably belonging to the genus Streptomyces. Colonies of strain #39 are white on solid medium. In liquid cultures containing yeast extract and glucose, in addition to baclofen, a slightly reddish pigmentation may be found in the supernatant fluid. Strain #39 was sent to two private laboratories for further identification based on fatty acid analysis. MICROCHECK, INC. (Northfield, Vt. 05663, U.S.A.) identified strain #39 as *Streptomyces halstedii olivaceus* with a similarity index of 0.435. ANALYTICAL SERVICES, INC. (Williston, Vt. 05495, U.S.A.) also identified strain #39 as S. halstedii olivaceus but with a similarity index of 0.307. Further identification of strain#39, using the 16 S ribosomal approach, identified strain#39 as *Streptomyces setonii*. People knowledgeable in the art of microbial identification generally assume that 16 S ribosomal analysis is more accurate than fatty acid analysis; for this reason, we tentatively identify strain#39 as an isolate of *Streptomyces setonii*. Stain #39 was deposited with the American Type Culture Collection (ATCC) on 19 Jun., 1996, and has been accorded Accession no. 55794.

The resolution potential of strain #39 was subsequently evaluated in small-scale fermentors using the pulse fed-batch approach. Efforts were spent at developing fermentation strategies that would increase significantly the enantiomeric excess (e.e.) of (R)-baclofen in the resulting supernatant fluids. Inoculum (strain #39) was prepared in shake flasks containing medium (Table 1) without baclofen but with glucose and yeast extract at 4 and 2 g/L, respectively. After about 72 h at 30° C., the inoculum was transferred (4% inoculum) into a small fermentor containing two liters of the same medium (without baclofen). The following initial fermentor conditions were used: 30° C., agitation at 350 rpm, pH maintained at 7, dissolved oxygen concentration at about 95% saturation, maintenance of dissolved oxygen concentration above 30% saturation using agitation. Fermentations were divided into two phases: a biomass accumulation phase (no baclofen) and a baclofen resolution phase. Periodic addition of a mixture of glucose and yeast extract was done during the two phases to increase biomass production and maintain viability. At the end of phase 1, biomass concentration varied greatly, from 1 to about 15 g/L (cell dry weight: dw); baclofen was subsequently added in a pulse fed-batch mode in amounts ranging from 0.05 to 1 g/L per pulse. As indicated earlier, a mixture of glucose and yeast extract was also added at the time of addition of baclofen. Culture samples were routinely withdrawn for the determination of the concentration of (R)- and (S)-baclofen and of other fermentation parameters such as biomass and glucose concentrations. Within about fifteen days (total fermentation time), enantiomeric excesses (e.e.) of (R)-baclofen superior to 90% were measured in the supernatant fluids as determined by chiral HPLC analysis (FIG. 1).

Example embodiments of the present invention are illustrated in the following examples.

EXAMPLE 1

Growth of strain #39 in defined medium containing racemic baclofen: Initial indications of stereoselectivity towards (S)-baclofen Three slants of complex medium (5 mL of medium in 15 mL-test tubes) containing baclofen at 0.25 g/L were inoculated with strain #39. The slants were incubated at 30° C. until such time that a lawn of growth appeared on the surface. Two of the three slants were sacrificed with the addition of 4 mL of a sterile saline solution (0.85% NaCl) and the resulting suspension was used as inoculum. Three 500 mL-Erlenmeyer flasks containing 100 mL of defined medium (Table 1, 0.25 g/L of baclofen) were inoculated with 1 mL of the above inoculum. The flasks were incubated for 9 days at 30° C. in an orbital shaker set at 200 rpm at which time a solution of yeast extract and glucose was added to each flask to give a final concentration of 2 and 4 gL, respectively. Incubation was continued for an additional 24 days. Samples were taken periodically to measure the concentration of both (S)- and (R)-baclofen and to perform microscopic observations. The samples were filter-sterilized using a Millex GS filter from Millipore. The filtrates were then analyzed by chiral HPLC to determine the concentrations of the two baclofen isomers. More detail on the chiral HPLC method used are given under EXAMPLE 4.

Figure 2:
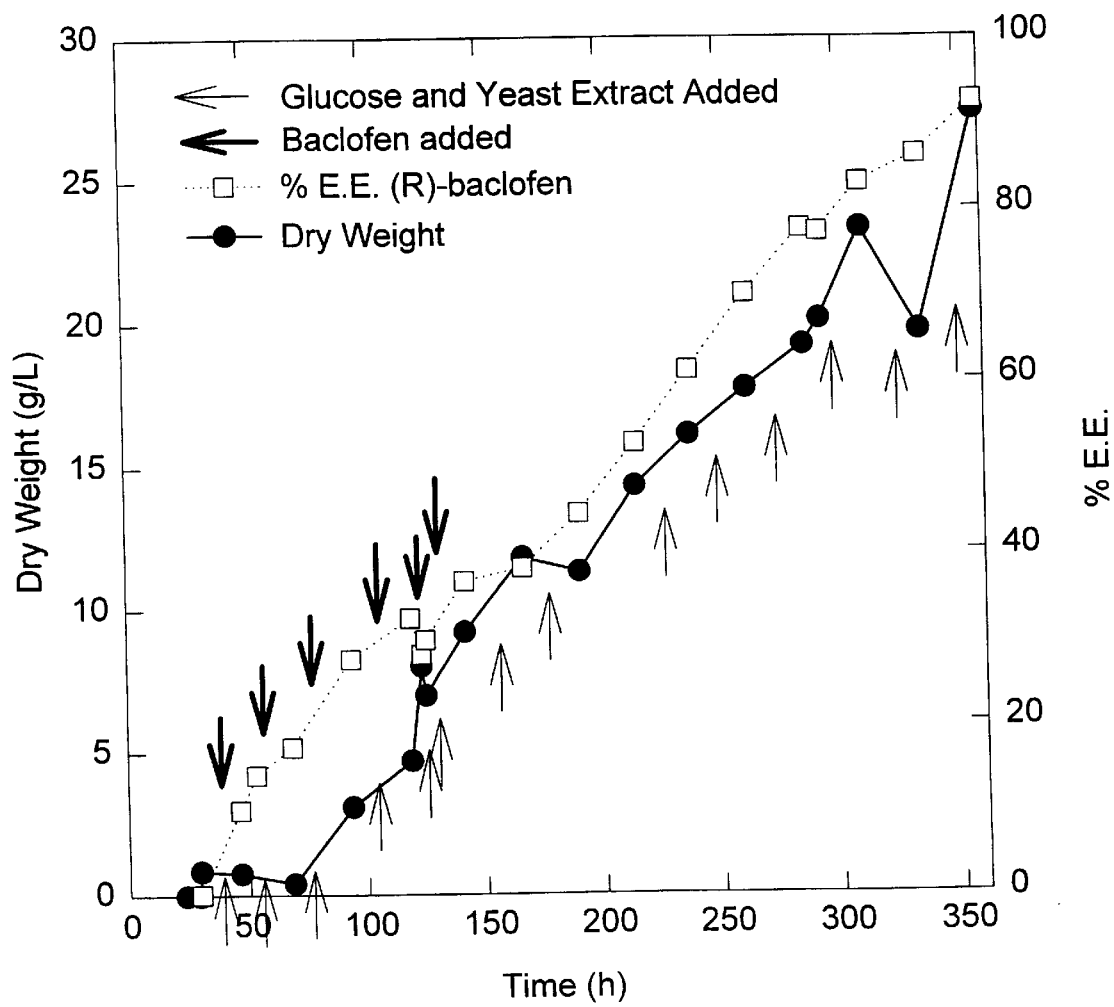
FIG. 2 is a graph illustrating the stereoselectivity of bacterial strain #39 towards (S)-baclofen.

A second shake flask experiment was done with a slight modification. Here, yeast extract and glucose were added to the flasks at the same time as the inoculum. The inoculated flasks were incubated for a total of 17 days with samples being taken periodically to follow the concentration of both baclofen isomers. The results of these two experiments are illustrated in FIG. 2. The results of the first experiment showed that the culture supernatant fluid contained an enantiomeric excess of (R)-baclofen calculated at 32% (e.e.) after 32 days. By comparison, the culture supernatant fluid from the second experiment contained an enantiomeric excess of (R)-baclofen calculated at 23% (e.e.) after 17 days of incubation.

EXAMPLE 2

Figure 3:
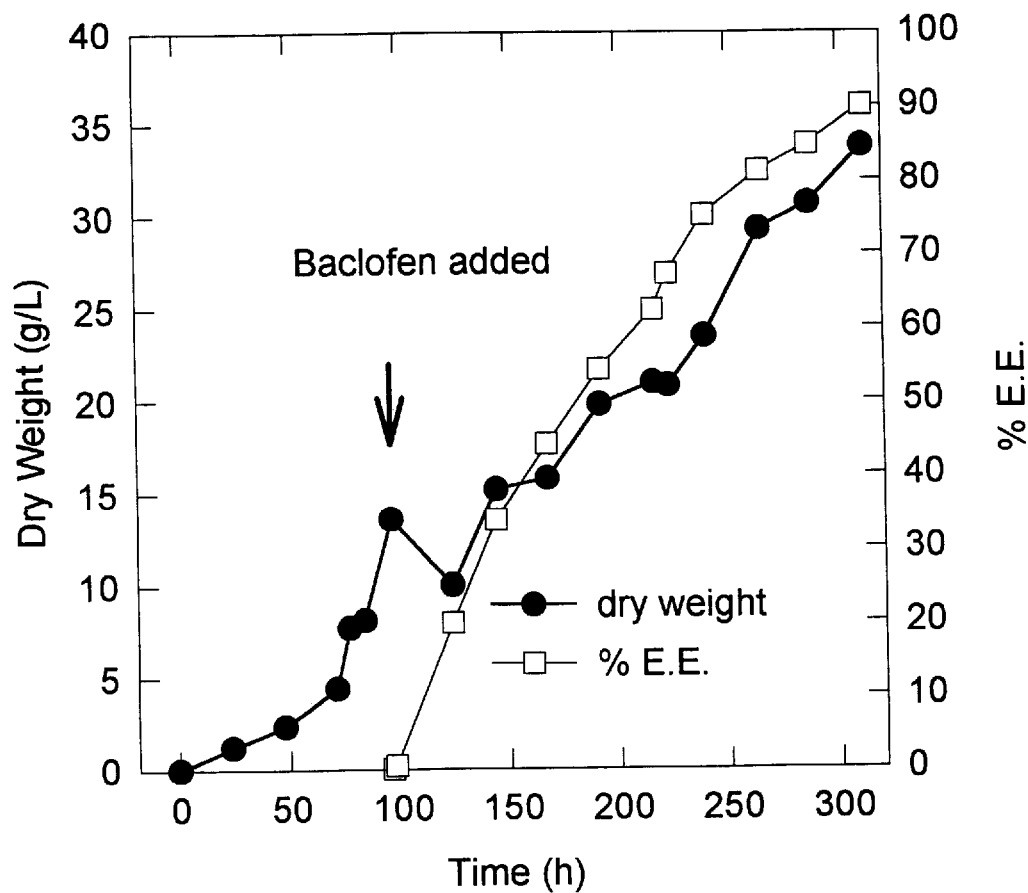
FIGS. 3 and 4 are graphs which illustrate the effect of pulse fed-batch addition of racemic baclofen and other nutrients, on the entantiomeric excess of (R)-baclofen.
Figure 4:
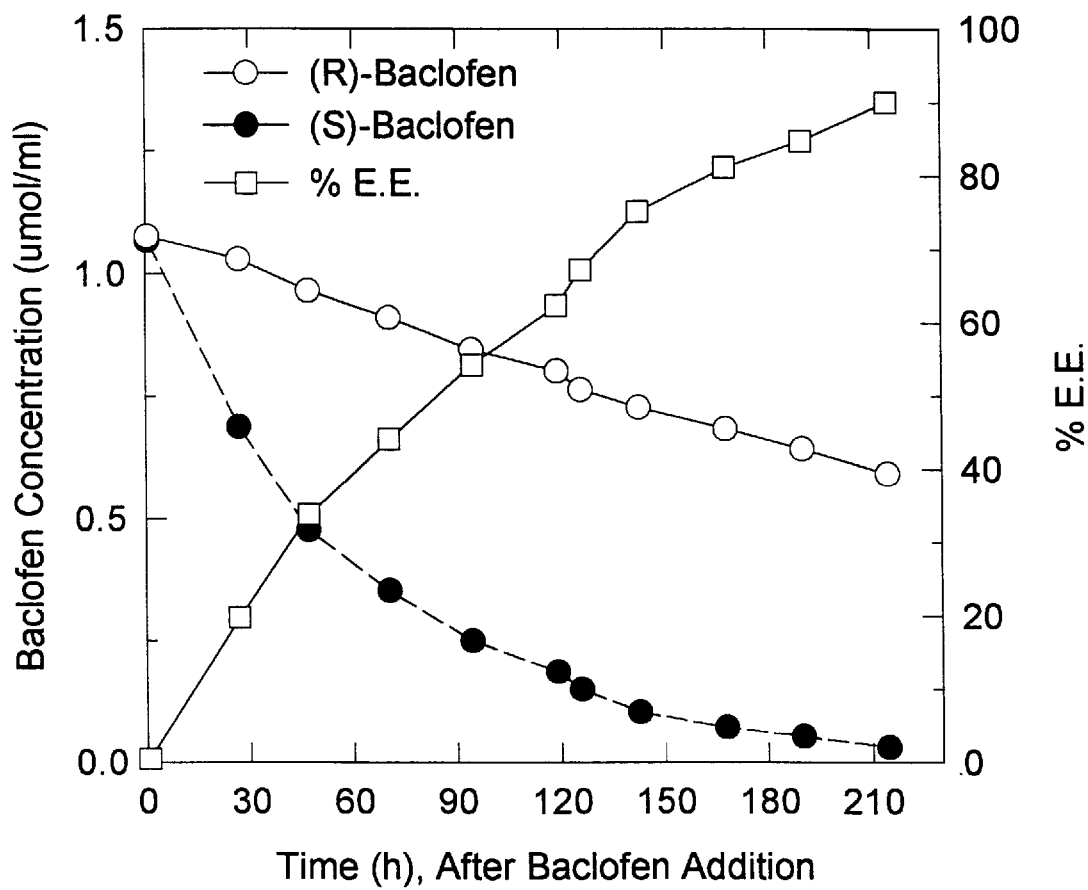

Growth of strain #39 in a 3.5 L-fermentor and pulse fed-batch addition of baclofen and other nutrients to increase the enantiomeric excess (e.e.) of (R)-baclofen in the resulting supernantant fluid Inoculum was obtained by transferring several colonies of strain #39 present on a Petri dish containing complex medium into a 500 mL-Erlenmeyer flask containing 100 mL of the same complex medium. The complex medium consisted of the defined medium of Table 1 with the addition of glucose and yeast extract at a final concentration of 4 and 2 g/L, respectively. The flask was incubated at 30° C. in an orbital shaker at 200 rpm for 3 days. The resulting cell suspension was added aseptically to 1.9 L of complex medium (same as above) in a 3.5 L Chemap fermentor. Temperature was maintained at 30° C. and pH was maintained at 7.0 with automatic addition of 2N $H_2SO_4$ or 2N KOH for an incubation period of 15 days. After 29 h of growth, a first addition of baclofen was done together with yeast extract and glucose (addition of 4 g of yeast extract, 8 g of glucose and 0.5 g of racemic baclofen). Throughout the fermentation, there was also periodic addition of baclofen (in amounts of 0.5 g for a total of 3.0 g) and of yeast extract and glucose (8 g of glucose+4 g of yeast extract per addition). Samples taken during the fermentation were assayed for cell-dry weight and examined microscopically. The remaining culture fluid from each sample was filter-sterilized (with a Millex GS filter from Millipore) and assayed for glucose concentration (using the Kodak IBI Biolyzer Rapid Analysis System) and the remaining filtrate was frozen at −20° C. until the end of the fermentation. At which time, the filtrate samples were thawed and assayed for the concentration of both (S)- and (R)-baclofen using chiral EPLC. Results indicated an enantiomeric excess of greater than 90% (e.e.) for (R)-baclofen at the end of the fermentation. Some of the results derived from this fermentation experiment are illustrated in FIG. 3. The results presented in FIGS. 3 and 4 are to show the same obvious results although the two experiments are not exactly the same. This increases our degree of confidence in the results, since we have arrived at the same conclusion using two "different" approaches.

EXAMPLE 3

Growth of strain #39 in a 3.5 L-fermentor: Build-up of biomass followed by batch addition of baclofen and other nutrients as a possible means to accelerate the resolution of racemic baclofen and consequently the production of (R)-baclofen from the racemic mixture A second fermentation using conditions similar to those described under EXAMPLE 2 was done to confirm the previous results. In this case, biomass was allowed to increase to approximately 15 g/L (cell-dry weight) by pulse addition of yeast extract and glucose (4 g and 8 g per addition, respectively) during the biomass accumulation phase. At that time, a solution of baclofen (1 g of baclofen) was added to the fermentor concomitant with a sterile solution containing 4 g of yeast extract and 8 g of glucose. Other fermentation conditions were essentially as above (EXAMPLE 2). Samples of the fermentation broth were taken to assay for glucose, (S)- and (R)-baclofen concentrations, and to follow cell-dry weight. Pulse addition of both yeast extract and glucose was continued until the enantiomeric excess of (R)-baclofen was greater than 90% (e.e.). The results of this fermentation are presented in FIG. 4. The concentration of each baclofen enantiomer was obtained by chiral HPLC analysis (as outlined in the text). Baclofen isomer verification was carried out for each HPLC chromatogram by subjecting the peaks of interest to PDA UV-spectrum matching against (R) and (S)-baclofen standards. UV traces of the peaks of interest for the entire fermentation fully matched with those for standard (R)- and (S)-baclofen.

EXAMPLE 4

Figure 5A:
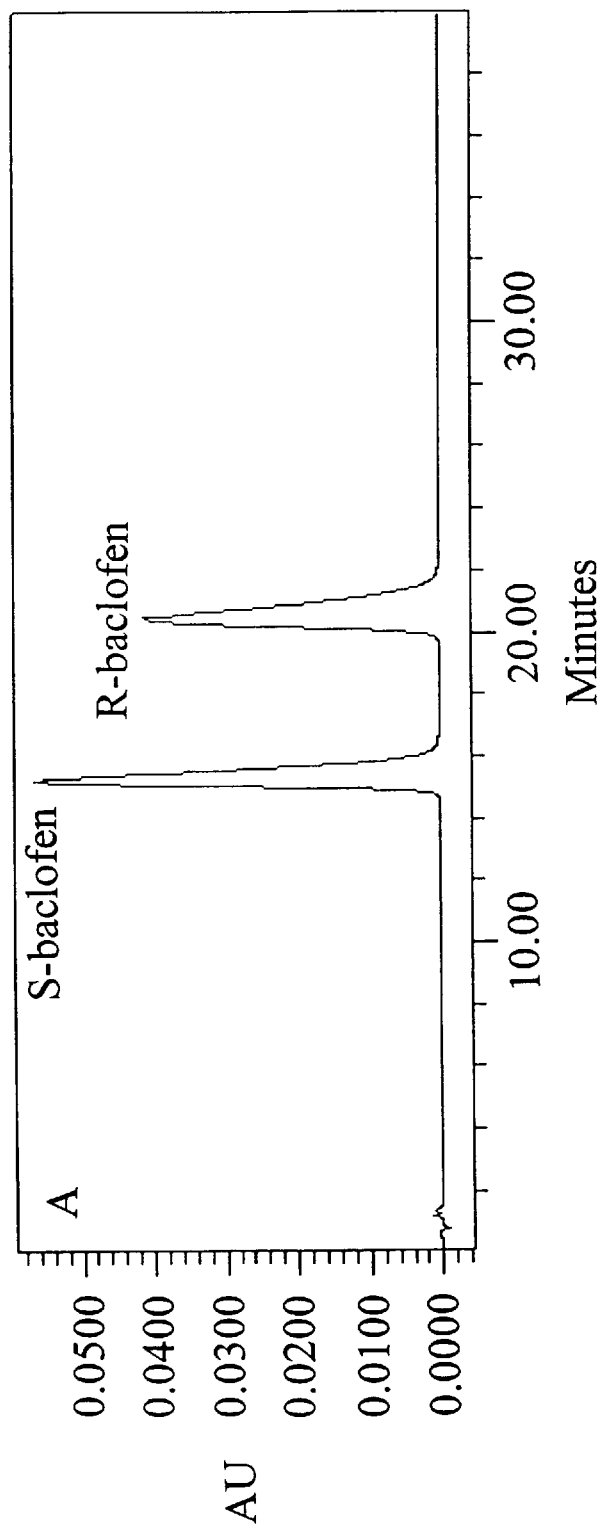
FIG. 5A is an HPLC chromatogram of standard racemic baclofen.
Figure 5B:
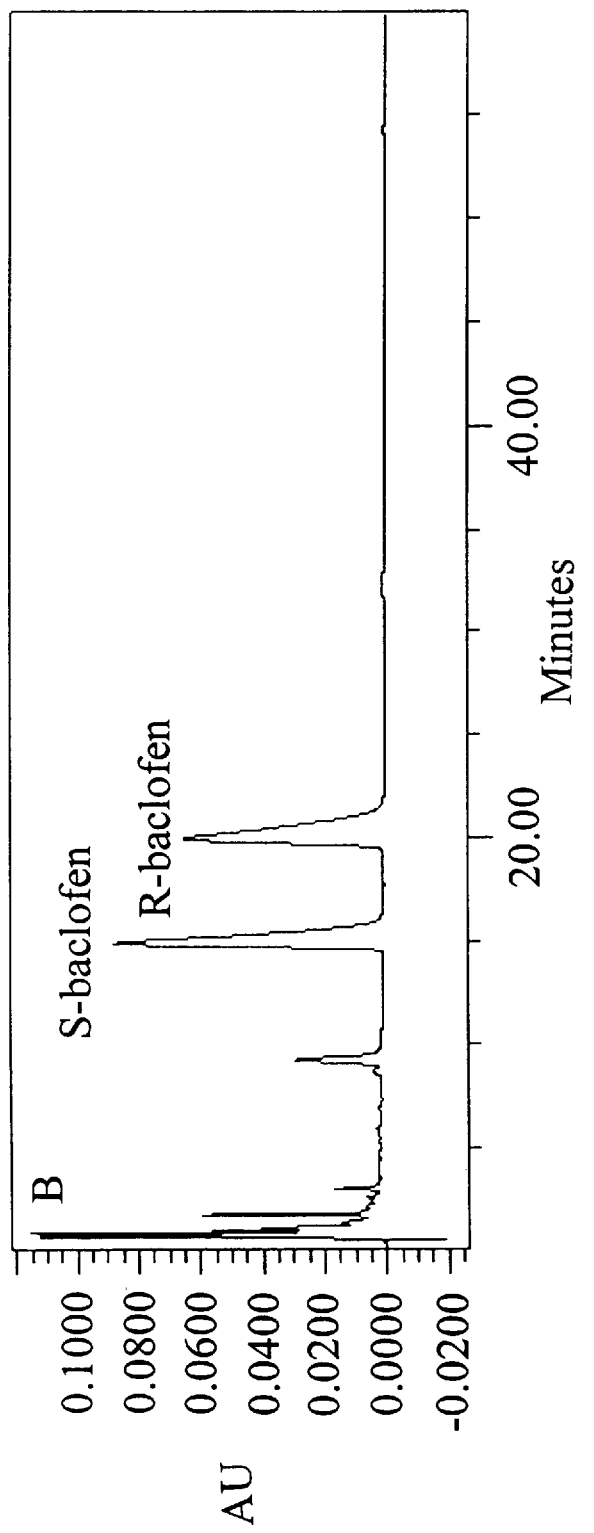
FIG. 5B is an HPLC chromatogram at the start of the baclofen resolution phase of the fermentation process.
Figure 5C:
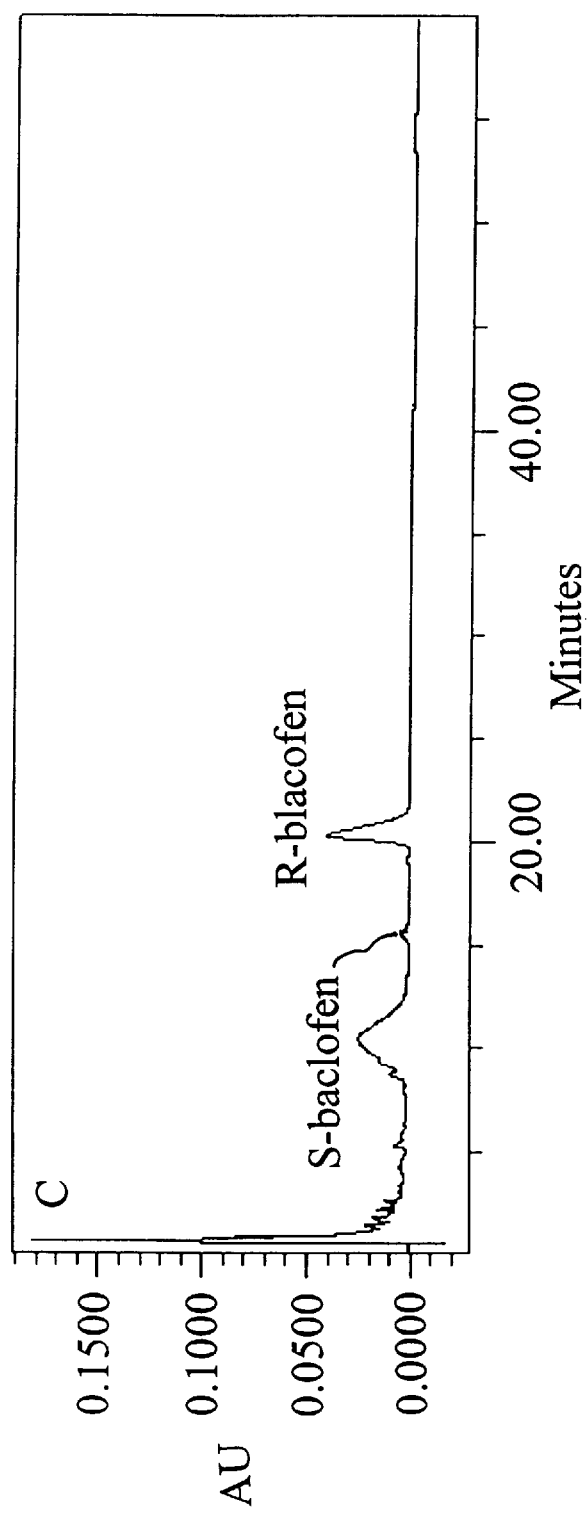
FIG. 5C is an HPLC chromatogram at the end of the baclofen resolution phase of the fermentation process.

Resolution of (S)- and (R)-baclofen by chiral HPLC: Analysis of representative fermentation samples A chiral HPLC method was first developed to resolve (S)- and (R)-baclofen. The following equipment was used: a Millennium 2010 system (Waters Scientific, Bedford, Mass.) run on a Digital Celebris 590 computer, a solvent delivery system (600 E), a sample processor (WISP 717) and a photodiode array detector (996 PDA). Calibration standards were prepared as follows: 0.2133 g of racemic baclofen was dissolved in 200 mL of mobile phase (0.01M trifluoroacetic acid). Subsequent dilutions in the same mobile phase were done to yield final concentrations of 12.5%, 25%, 50% and 75% of the initial standard solution. Separation of the baclofen enantiomers was accomplished via HPLC analysis using the following chiral column: Crownpak CR(+)m 0.4 cm×15 cm (Chiral Technologies Inc., Exton, Pa.). The flow was maintained constant at 2.0 mL/min, the column temperature was 40° C. and an injection volume of 10 μL was used for standards and fermentation samples. The chromatograms were scanned from 200 to 280 nm with 1.2 nm resolution. The extracted wavelength of 220 nm was used for quantitation. The retention times of (S)-baclofen and of (R)-baclofen were 15.5 and 19.5 minutes, respectively. FIG. 5(A) shows a typical chromatogram obtained after resolution of standard racemic baclofen. FIG. 5(B) shows a typical chromatogram of a fermentation broth containing racemic baclofen taken at the start of the fermentation resolution phase. Finally, FIG. 5(C) shows a typical chromatogram of a fermentation broth taken at the end of the fermentation resolution phase.

We claim:

1. A process for the production of a substantially isomerically pure isomer of a compound of structural formula II

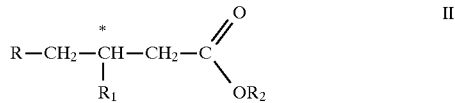

wherein R is $NH_2$ or substituted $NH_2$, $R_1$ is phenyl or p-halo-substituted phenyl, $R_2$ is H, lower-alkyl, $NH_2$, Cl, or a metal salt thereof and C* is a chiral carbon, comprising contacting a racemic mixture of the (R)- and (S)-isomers of a compound of formula II, with a biologically purified microorganism, identified as *Streptomyces halstedii* strain no. 39, ATCC Deposit Accession No. 55794 or the cell-free enzymes derived therefrom, in a suitable aqueous culture medium, to selectively metabolize one of the isomers, while having minimal activity on the other isomer, and recovering the substantially isomerically pure unreacted isomer.

2. A process according to claim 1, wherein the pH is between 5.5 and 7.5.

3. A process according to claim 2, wherein the temperature is between 20° and 35° C.

4. A process according to claim 3, wherein the culture medium includes 0.1 to 2 g/L of the racemic mixture.

5. A process according to claim 4, wherein the culture medium also includes about 4 g/L of glucose and about 2 g/L of yeast extract.

6. A process according to claim 5, wherein the microorganism or the cell-free enzymes derived therefrom are either in the free or immobilized state.

7. A process according to claim 1, wherein R is $NH_2$.

8. A process according to claim 7, wherein $R_1$ is p-halo-substituted-phenyl.

9. A process according to claim 8, wherein halo is chloro.

10. A process according to claim 9, where $R_2$ is H.

11. A biologically purified culture of a Streptomyces microorganism identified as *Streptomyces halstedii* strain no. 39, ATCC Deposit Accession No. 55794 and enzymes derived therefrom.

12. A biologically purified microorganism, identified as *Streptomyces halstedii* strain no 39, ATCC Deposit Accession No. 55794.

13. In a fermentation or bioconversion process, using the microorganism of claim 12 or the cell-free enzymes derived therefrom, for the microbial and/or enzymatic resolution of a racemic mixture of compounds of formula II as defined in claim 1.

14. A process according to claim 13, wherein the microorganism or the cell-free enzymes derived therefrom, are either in the free or immobilized state.

15. A process according to claim 14, wherein structural formula II, R is $NH_2$, $R_1$ is p-chloro-phenyl and $R_2$ is H.

* * * * *